United States Patent [19]

Weinstein

[11] Patent Number: 4,781,590

[45] Date of Patent: Nov. 1, 1988

[54] DENTAL INSTRUMENT

[75] Inventor: Naomi J. Weinstein, Long Beach, Calif.

[73] Assignees: Anthony Horowitz, a part interest; Robert F. Senescu, both of Van Nuys, Calif. ; a part interest

[21] Appl. No.: 915,993

[22] Filed: Oct. 3, 1986

[51] Int. Cl.⁴ .............................................. A61C 3/06
[52] U.S. Cl. .................................................. 433/142
[58] Field of Search ............... 433/141, 142, 143, 146

[56] References Cited

U.S. PATENT DOCUMENTS

| | | | |
|---|---|---|---|
| 1,202,698 | 10/1916 | Ford | 433/142 |
| 2,245,291 | 6/1941 | Myerson | 433/141 |
| 3,267,623 | 6/1966 | Block | 433/142 |

Primary Examiner—Robert Peshock
Attorney, Agent, or Firm—Jack C. Munro

[57] ABSTRACT

An instrument usable in the dental field to facilitate smoothing of restorations and cleaning of teeth. The instrument comprises of an elongated handle upon which is mounted a head at one end. The head has an operating surface which is located transverse to the elongated axis of the handle. A pad is to be removably secured to the operating surface. The outer surface of the pad includes an abrasive material.

3 Claims, 1 Drawing Sheet

DENTAL INSTRUMENT

BACKGROUND OF THE INVENTION

The field of this invention relates to an instrument to be usable by a dentist to smooth restorations and by a dental hygienist for the removing of foreign material on one's teeth.

Within dentistry, the use of restorations is exceedingly common. During the installing procedure of the restoration, it is necessary to smooth the subgingival structure of the restoration. At the present time, the devices used to smooth restorations take either the form of a high speed instrument (such as a drill) that utilize metallic burring bits or a disc which is driven at a slow speed (again by a drill). Both the bit or the disc is utilized to trim the flash of the restoration. Also, a common form of another abrading device is a sheet material strip wherein the opposing surfaces of the material strip include a sandpaper type of surface. These sandpaper strips are used manually by the dentist in order to effect smoothing of the restoration.

The use of the burring bits, sandpaper discs and strips inherently cause gingival bleeding and thus trauma to the tissue. The addition of blood will result in wetting of the tooth surface and the restoration and thusly contaminates the smoothing procedure. Also, the creation of the blood and saliva tends to prevent adhesion of the restoration to the teeth. Generally, the restoration is applied as a soft material which is then caused to adhere and harden.

In the field of professional dental care, there is also a need to utilize a tool to facilitate the removing of plaque and other accumulated foreign material from a person's teeth.

SUMMARY OF THE INVENTION

The primary objective of the present invention is to construct a dental instrument which includes an abrasive pad wherein this abrasive pad can be utilized in almost every area of one's teeth and its usage can be precisely controlled.

Another objective of the present invention is to construct an instrument which can be easily slipped below the gum line to quickly smooth the subgingival portion of a restoration without damaging gum tissue.

Another objective of the present invention is to construct an instrument which causes substantially no bleeding to occur during its usage permitting the dentist to have greater visibility so that voids within the restoration can be quickly ascertained and repaired and also the dentist is able to avoid "dishing out" of the restoration by excessive removal of a portion of the restoration.

Another objective of the present invention is to smooth the restoration so that it can follow the slight convex shape of the tooth and therefore prevent any gingival irritation.

Another objective of this invention is to provide an instrument which can be used by the dental hygienist to remove obvious excess composite restoration if noted during the routine cleaning procedure of the hygienist. Usually an area of irritation can easily be noted by observing localized redness of the tissue at the area of the composite restoration.

The structure of the present invention comprises an elongated manually graspable handle. To one end of this handle is attached a head. This head has an outer planar operating surface the overall configuration of which is triangular. Onto this operating surface is to be removably attached a sandpaper type of pad. The configuration of the pad matches the configuration of the operating surface, that being triangular. Various grit types of pads could be utilized. After each usage, the pad is removed and replaced with a new pad.

DETAILED DESCRIPTION OF THE SHOWN EMBODIMENT

Figure 1:
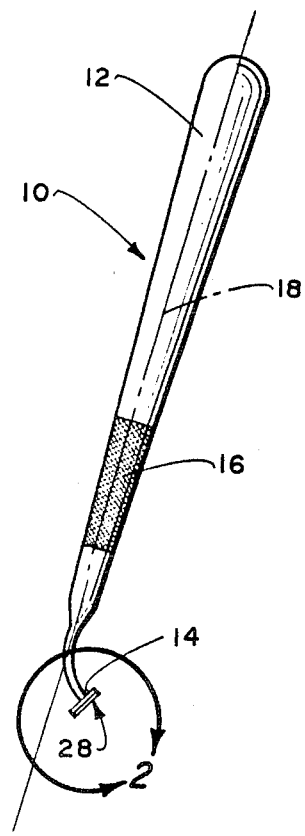
FIG. 1 is an isometric view of the dental instrument of the present invention.

Referring particularly to the drawing there is shown the dental instrument 10 of this invention which is composed of an elongated rigid, metallic, handle 12. The outer end of the handle 12 is free with the inner end of the handle 12 being integrally attached to a head 14. The head 14 will normally be composed of a material the same as handle 12. The handle 12 will include a knurling 16 on its outer surface to facilitate handling.

The exterior, free surface of the head 14 is planar. This surface is defined as an operating surface 16. Although this surface 16 is shown planar, it is considered to be within the scope of this invention that the surface could be slightly arcuate.

Figure 2:
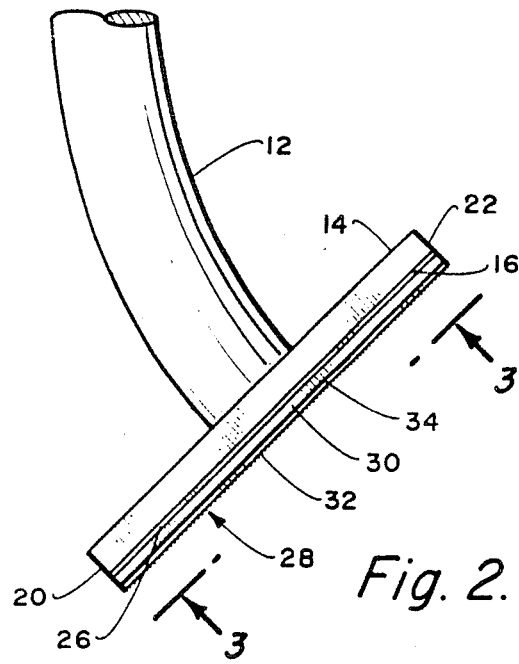
FIG. 2 is an enlarged view of the head section of the dental instrument of FIG. 1 taken along line 2—2 of FIG. 1.
Figure 5:
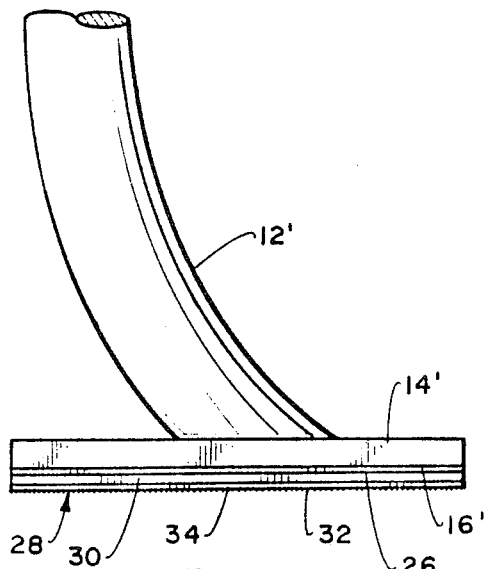
FIG. 5 is a view similar to FIG. 2, but of a modified form of head which is located at a different angular location relative to the handle.
Figure 4:
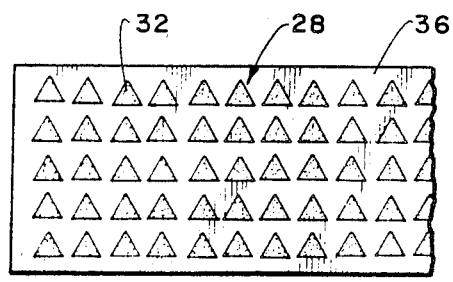
FIG. 4 is an elevational view of the carrier strip upon which are located a plurality of pads which are to be removable therefrom to be utilized in conjunction with the dental instrument of this invention.

As shown in FIG. 2 of the drawing the surface 16 is substantially inclined to the longitudinal center axis 18 of the handle 12. This surface 16 could be oriented at a different position, if such is desired, as is shown by surface 16' in FIG. 5. This orienting at a different position is achieved by connecting of the head 14' at a less inclined angular relationship relative to the handle 12'.

Figure 3:
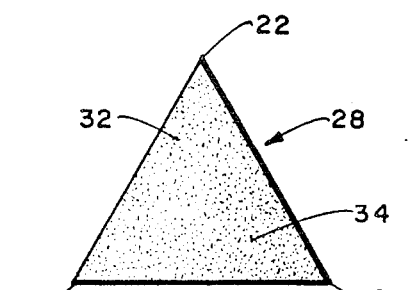
FIG. 3 is a plan view of the head portion of the dental instrument of this invention taken along line 3—3 of FIG. 2.

Referring in particular in FIG. 3 of the drawing, the overall configuration of the head 14 is shown to be triangular forming corners 20, 22 and 24. These sharp pointed corners 20, 22 and 24 facilitate usage of the instrument 10 in hard to reach areas within one's teeth such as under the gum or between teeth.

Adhesively secured to the operating surface 16 or 16' by an adhesive layer 26 is a pad 28. The overall configuration of the pad 28 is basically identical to the overall triangular configuration of the operating surface 16 or 16'. The pad 28 will generally be composed of a sheet material such as a paper or plastic layer 30. The adhesive layer 26 is fixed to the backside of the layer 30.

On the front side of the layer 30 there is placed a coating 32. The coating generally will take the form of a resin or adhesive within which has been located a mass of grit 34. The grit 34 will usually take the form of a fine sand type of material and may also include finely ground walnut shells or other similar type of material. The grit will be evenly dispersed within the coating and when applied onto sheet material layer 30 of the pad 28, the coating will then harden at which time the pad 28 is ready for use.

It is to be understood that each dental instrument 10 will be utilized with a substantial number of pads 28. In order to provide a substantial number of the pads 28 to be ready for usage, the pads 28 are to be mounted on a release paper 36. The pads 28 are removed one at a time and placed on the operating surface 16 or 16'. After a single usage it is intended for the used pad 28 to be removed and discarded with a new pad 28 being again located on the operating surface 16 or 16'.

What is claimed is:

1. A dental instrument adapted to be used manually comprising:

a handle adapted to be grasped for usage by the user, said handle being elongated defining an aft end and a fore end, said handle having a longitudinal center axis, said aft end being free;

a head attached to said fore end, said head having an operating surface, said operating surface being substantially located within a single plane said operating surface being planar, and the overall configuration being triangular, said single plane being inclined to said longitudinal center axis; and a sheet material pad having a front surface and a rear surface, an abrasive layer attached to said front surface, an adhesive layer attached to said rear surface, said adhesive layer to connect with said operating surface to temporarily secure said pad onto said operating surface, said pad being removable and replaceable from said operating surface.

2. The dental instrument as defined in claim 1 wherein:

said pad having an overall triangular configuration.

3. The dental instrument as defined in claim 1 wherein:

said operating surface being spaced from said longitudinal center axis.

* * * * *